United States Patent
Lingo, Jr. et al.

(10) Patent No.: US 6,626,845 B2
(45) Date of Patent: Sep. 30, 2003

(54) METHOD AND APPARATUS FOR MEASUREMENT OF IN VIVO AIR VOLUMES

(75) Inventors: Lowell Edwin Lingo, Jr., Morrisville, NY (US); Rick Morris Roark, Vega, TX (US)

(73) Assignees: New York Medical College, Valhalla, NY (US); DFI Enterprises, Inc., Morrisville, NY (US)

( * ) Notice: Subject to any disclaimer, the term of this patent is extended or adjusted under 35 U.S.C. 154(b) by 0 days.

(21) Appl. No.: 09/828,085

(22) Filed: Apr. 6, 2001

(65) Prior Publication Data

US 2001/0037071 A1 Nov. 1, 2001

Related U.S. Application Data

(60) Provisional application No. 60/195,212, filed on Apr. 7, 2000.

(51) Int. Cl.$^7$ ................................................ A61B 5/091
(52) U.S. Cl. ........................ 600/538; 600/533; 600/540
(58) Field of Search ................................. 600/528, 533, 600/538, 540, 541, 542

(56) References Cited

U.S. PATENT DOCUMENTS

| | | | | |
|---|---|---|---|---|
| 3,319,624 A | * | 5/1967 | Arp et al. | 600/541 |
| 3,559,638 A | * | 2/1971 | Potter | 600/540 |
| 3,675,640 A | | 6/1972 | Gatts | 128/2.05 R |
| 4,802,492 A | | 2/1989 | Grunstein | 128/720 |
| 4,844,085 A | * | 7/1989 | Gattinoni | 600/533 |
| 5,211,180 A | * | 5/1993 | Wright et al. | 600/538 |
| 5,513,648 A | | 5/1996 | Jackson | 128/721 |
| 5,575,283 A | | 11/1996 | Sjoestrand et al. | 128/204.23 |
| 5,857,459 A | | 1/1999 | Snow et al. | 128/204.21 |
| 5,876,352 A | * | 3/1999 | Weismann | 600/529 |
| 5,937,854 A | * | 8/1999 | Stenzler | 128/204.18 |
| 6,139,506 A | | 10/2000 | Heinonen et al. | 600/532 |
| 6,183,423 B1 | | 2/2001 | Gaumond et al. | 600/529 |

* cited by examiner

*Primary Examiner*—Stephen M. Hepperle
(74) *Attorney, Agent, or Firm*—Cheryl H. Agris

(57) ABSTRACT

This invention relates to instruments, particularly medical and research instruments that are used for assessing gas volumes of cavities, particularly, cavities that may exhibit a compliance to changes in pressure, such as in vivo volumes of the lung, thorax, oropharynx and/or nasopharynx.

18 Claims, 3 Drawing Sheets

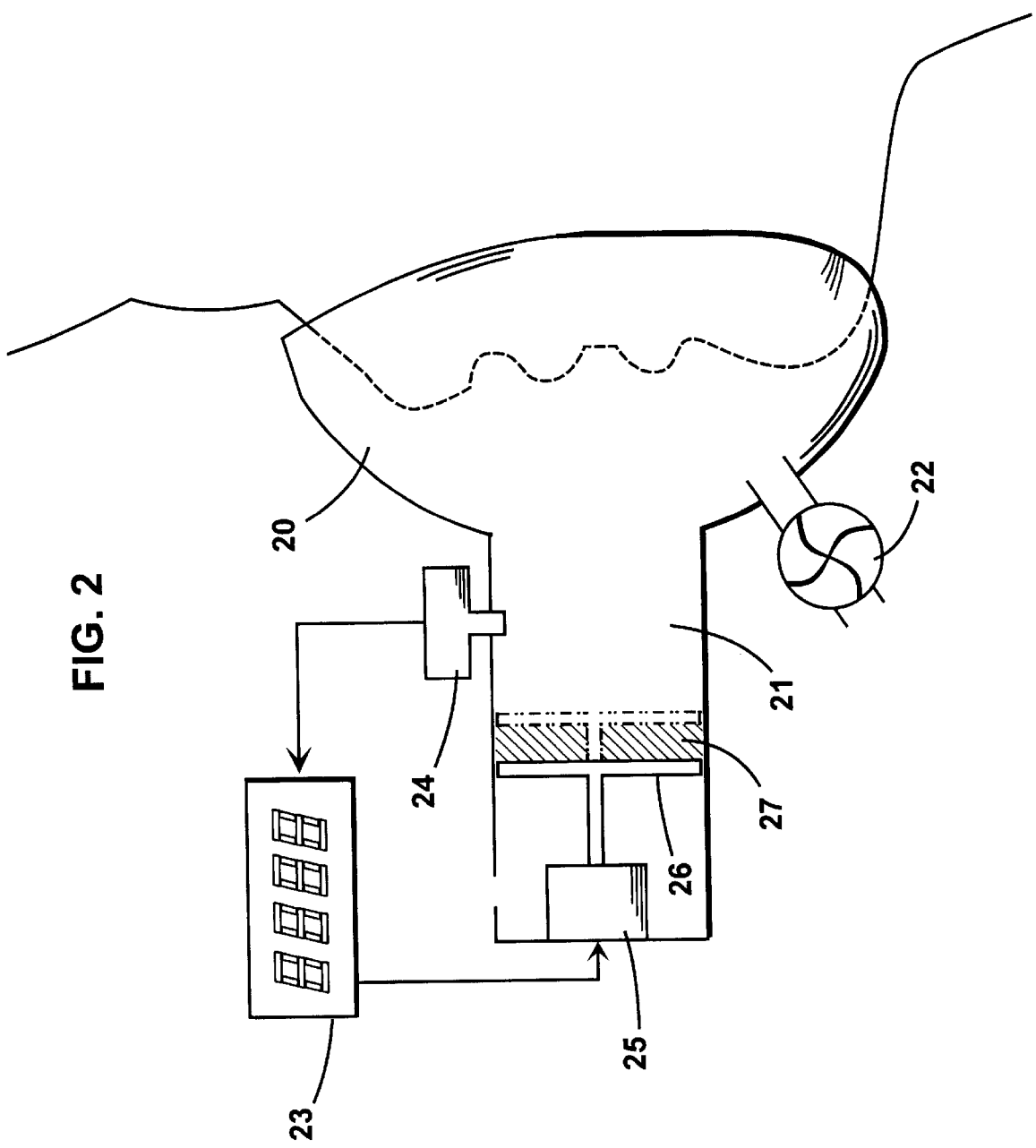

METHOD AND APPARATUS FOR MEASUREMENT OF IN VIVO AIR VOLUMES

PRIORITY CLAIM

This application claims priority from U.S. provisional application serial No. 60/195,212, filed Apr. 7, 2000, the contents of which are incorporated herein by reference.

FIELD OF THE INVENTION

This invention relates to instruments, particularly medical and research instruments that are used for assessing gas volumes of air cavities, particularly, air cavities that may exhibit a compliance to changes in pressure, such as in vivo volumes of the lung, thorax, oropharynx and/or nasopharynx.

BACKGROUND OF THE INVENTION

Over the years, a number of methods have been used to determine the functional residual capacity (FRC) of the lung and related thoracic gas measures of a patient. These methods have involved gas dilution techniques, body plethysmography, and radiographic techniques. Gas dilution techniques require the patient to inhale special gases and necessitate special ventilation facilities (see, for example, U.S. Pat. No. 6,139,506). Radiographic techniques require a patient to be exposed to radiation. Additionally, static chest wall and abdominal composure by the patient is required during imaging. Plethysmography requires enclosing the patient or most of the patient's body (see, for example, U.S. Pat. Nos. 5,513,648 and 5,159,935) in a sealed enclosure or at the very least outfitting the patient with impedance belts about the torso (see, for example, U.S. Pat. No. 5,857,459). For these methods, lung pressurization maneuvers are performed by the patient during which changes in lung volume are simultaneously assessed by the plethysmograph. The general gas equation, relating pressure and volume and changes in pressure and volume, is used to determine the unknown volume. Current plethysmographic techniques to assess thoracic gas volume suffer from artifacts due to stomach gas, which causes compliance during testing maneuvers.

A method to estimate "trapped" air volume (not absolute volume) in lung of paralyzed patients has been proposed by obtaining a volume/pressure curve upon forced ventilation of the patient's lung (see U.S. Pat. No. 4,844,085). The large volume of gas exchange with this method introduces errors that must be compensated and the forced pressurization/depressurization precludes normal breathing of the patient during testing. None of the above methods allow convenient isolation and measurement of the volume of the oral cavity and nasal pharynx.

U.S. Pat. No. 5,937,854 discloses a method and apparatus for ventilator pressure and optimization by administering fixed stepwise pressure changes to the lungs of a patient and measuring the lung volume change resulting from each pressure change. The lung volume change is measured by using the RIP technique. This utilizes two elastic cloth bands containing insulated wires, which encircle the patient's rib cage and abdomen and are connected to an oscillator module.

OBJECTS AND ADVANTAGES

It is accordingly a principal object of the present invention to provide a non-invasive device and method for measuring in vivo gas volumes of a patient, including lung and pharyngeal volumes and, particularly, to obtain volume measurement in the presence of compliance.

An additional object of the present invention is to provide an inexpensive device and method that measures the lung volume of a patient independent of a sealed chamber or ventilated airspace and that does not require outfitting the patient with respiratory bands.

A further object of the present invention is to provide a device and method to measure lung and airway volume of a patient by a means that is not dependent upon patient cooperation and participation. In other words, the patient is only required "to breathe" and not to perform specialized pressurization maneuvers to within a certain tolerance. Therefore yet another object of the present invention is to provide a device for measuring the lung volume of the immobile, paralyzed, and "intensive care" or "special care" patient.

Accordingly, as will be disclosed in detail below, several advantages of the present invention are the measurement of in vivo volumes with a device that is smaller and more portable than existing systems, a device and method that is less complicated for clinicians and less troublesome for patients, and a device and method that serves a greater patient population, including veterinary applications, than is heretofore possible.

SUMMARY OF THE INVENTION

The purpose of the present invention is to provide a non-radiographic, noninvasive, portable, and non-confining apparatus for measuring gas volumes of in vivo cavities, including but not limited to lung volume and volumes of the thorax, oral and nasal pharynx. Further, the apparatus does not require sophisticated lung pressurization maneuvers to be performed by the patient or the outfitting of patients with thoracic position transducers. The present invention is intended therefore to serve a comprehensive patient population, including the bedridden, unawake, paralyzed, and sedated patient. Further, the device does not require the patient to inhale special gases or be subjected to imaging radiation.

It is recognized that various methods exist for assessing lung volume. The present invention represents improvements in the apparatus of boxless measurement of lung volume that can take the form of several embodiments. The detailed embodiments described herein are taken as representative or exemplary of those in which the improvements of the invention may be incorporated and are not presented as being limited in any manner.

The invention is directed to an apparatus for measuring gas volumes of an in vivo cavity of unknown compliance in a subject, particularly a patient comprising:

(a) an air cavity with induction means for inducing calibrated volume changes in said air cavity;

(b) a means for interfacing said air cavity to the in vivo volume of the subject to be measured;

(c) a means connected to said air cavity for measuring air pressure variations; and (d) a control means electrically coupled to said induction means and measuring and processing means for calculating the gas volume in said subject.

In one embodiment, the subject is a human patient; in another embodiment the subject is a mammal; in yet another embodiment, the subject is a non-living item with a cavity exhibiting compliance, such as a balloon, a tank containing a bladder, or a tank with an inverted floating cover such as one used to contain hydrogen or natural gas.

The apparatus interfaces an air cavity to particularly the patient by means of a facial mask, nasal mask, mouthpiece or tubes. In a preferred embodiment, the interfacing means is a facial mask so that a common air cavity is formed with the patient via the oral and/or nasal orifices. The apparatus includes a respiratory access valve connected to its inner cavity that, when open, permits the patient to exchange air with the external environment in the manner of ordinary breathing (means for interfacing said air cavity to ambient environment) and, when closed, permits artificial pressurization of the cavity by means of a calibrated volume-changing piston (means for inducing volume change). The apparatus includes a calibrated device to assess air pressure changes occurring inside the common air cavity and a device to assess air pressure of the ambient environment.

The valve interfaces between the external environment and the inner cavity of the apparatus, and is opened or closed by passive means according to breathing airway pressure of the patient. The valve is constructed in such a manner as to remain open while the patient is in the process of inhaling or exhaling, and to momentarily close during the period of time that the patient is changing breathing modality from exhalation to inhalation, when cavity pressure is beneath the shutter threshold. The pressure change in the system due to the induced change in volume is, in itself, insufficient to open the valve.

The invention is also directed to a method for measuring a gas volume of an in vivo cavity in a subject utilizing the apparatus of the present invention comprising (a) attaching said apparatus to said subject;
(b) measuring the barometric pressure in an area near the subject;
(c) measuring changes in induced pressure and volume in said cavity during an induction and preferably at least two inductions, and
(d) calculating said gas volume.

The method may further comprise the step of calculating compliance of said cavity where compliance is present.

The control and processing unit monitors system pressure during the breathing cycle and is therefore programmed to determine if pressure is negative (indicating inhalation), positive (exhalation), or zero (peak of inhalation or trough of exhalation). When the processing and control unit assess that air cavity pressure is within the range that the respiratory valve has become closed and, further, that the breathing cycle is at the trough of exhalation, the control unit repositions the piston and thereby decreases the system volume by a small, known amount. Those versed in the art comprehend that pressure and volume of gas in a closed mass system are mathematically related by the general gas equation. Specifically, the pressure-volume product of the system gas prior to piston movement is equal to the pressure-volume product after piston movement, for the same gas temperature.

Compliance occurs whenever the volume under test changes as a result of increased inner forces due to pressurization of the air cavity. Possible sources of compliance are cheeks and lung wall. Of particular note is compliance of the lung wall due to stomach gas, which is an artifact of body plethysmography of all types. Those versed in the art will appreciate the difficulty of measuring a volume under the circumstances in which that volume might adjust itself to the increased pressure created by the measurement process. The invention proposes a means of determining compliance in the course of testing by applying a plurality of different induced gas volumes that result in different pressure measurements from which in vivo volume may be determined.

BRIEF DESCRIPTION OF THE DRAWINGS

FIG. 2 shows a typical embodiment of the invention.

DETAILED DESCRIPTION OF THE INVENTION

Figure 1A:
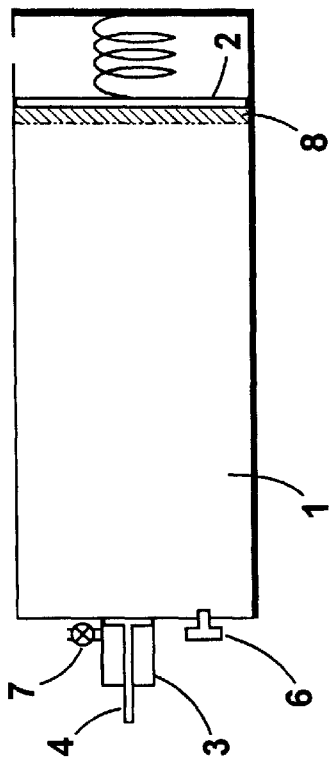
FIGS. 1A to 1D schematically show the invention in the various states of its operational cycle as described herein in the EXAMPLES.

To enhance understanding of the present invention, it is noted here that the formulae used to determine system volume are identical to those used by the clinically prevalent method of whole body plethysmography. In the case of whole body plethysmography, a change in system volume is created by the patient, by panting against a valve that has been closed at the trough of inhalation during a normal breathing cycle. The resulting changes in lung volume that occur during the panting maneuver are determined by solving a similar formula for the closed air cavity that exists between the patient and the inner box. The estimates of volume change thus obtained are used in the gas-volume equation to determine an estimate of lung volume. In the case of the present invention, the change in induced volume is known precisely since it is supplied in metered portions to the in vivo volume under test, and does not require estimation by a separate plethysmograph. Thus, patient participation and cooperation is minimized in the present invention when testing for thoracic gas volume.

In a typical embodiment, the apparatus shown in FIG. 2 is interfaced to the patient, with facemask 20 forming an airtight seal between the inner cavity of the apparatus 21 and in vivo air volume of the patient. Normal breathing by the patient is vented through valve 22. Valve 22 interfaces between the external environment and inner cavity 21 of the apparatus and is opened or closed by passive means according to breathing pressure of the patient.

The processing and control unit 23 monitors the pressure of the system via pressure transducer 24. The processing and control unit (PCU) also drives linear motor 25 at the appropriate time to move piston 26 a calibrated amount. Pressure changes monitored by transducer 24 from two or more system cycles are processed by PCU 23 as described in the EXAMPLES to display the calculated volume and compliance.

Figure 3:
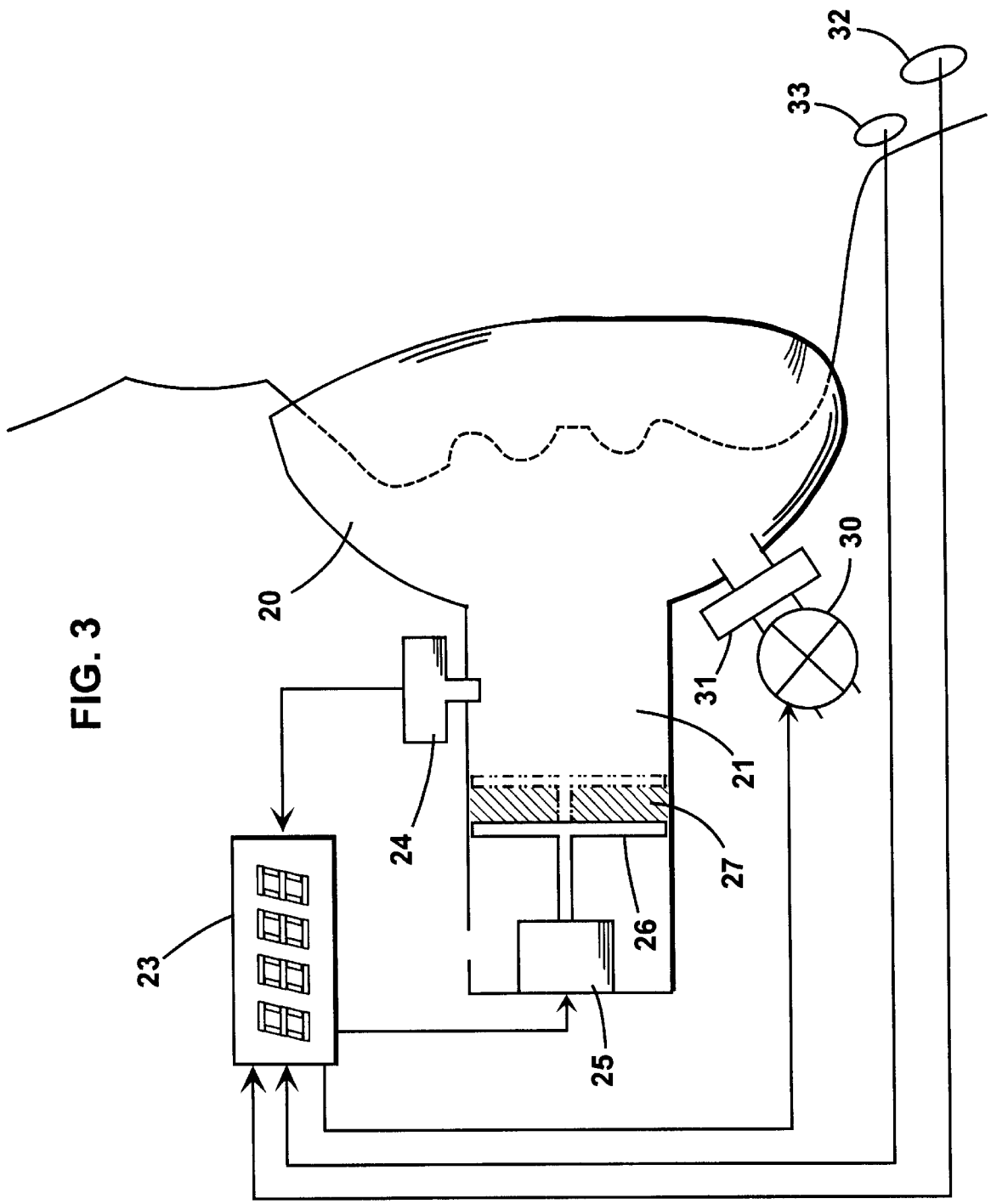
FIG. 3 shows a second embodiment of the invention with added monitoring components.

In an alternative embodiment shown in FIG. 3, a valve 30 controlled by PCU 23 replaces passive valve 22 shown in the embodiment of FIG. 2. A control signal from PCU 23 signals the valve to vent the apparatus cavity to atmosphere when a preset differential pressure between system and atmosphere exists. This differential pressure is created by a pneumotach screen 31 located in the air stream of valve 30. A pulse monitor 33 interfaces to PCU 23 allowing each induced volume change to occur at the same phase in the heart cycle.

Pneumotach screen 31 serves a further purpose in the alternative embodiment. It may be desirable to obtain measurements of volume at successively occurring troughs of the breathing cycle to enhance accuracy via signal averaging. However, the amount of air in the lungs at the trough of the breathing cycle, FRC, is slightly different for each cycle, even during ordinary breathing. Pneumotach screen 31 and differential pressure transducer 24 permit measurement of volumetric air flow during breathing, so that corrections to lung volume $V_0$ can be made during the averaging process. Volumetric air flow measurements via pneumotach screen 31 and differential pressure transducer 24 are calibrated prior to patient testing using known air flow values and other standards common to the industry. Therefore, the apparatus of the present invention further comprises means for measurement of volumetric air flow during breathing.

EXAMPLES

To facilitate understanding of the operation of the invention, a schematic drawing of a general embodiment of the invention is shown in FIGS. 1A to 1D. The apparatus is shown interfaced to an air cavity 1 of unknown volume $V_0$ to be determined, containing a compliant wall 2 shown figuratively as a movable piston backed by a spring. A cylinder 3 fitted with, for example, a piston 4 contains a pre-determined volume 5 that communicates with air cavity 1. The induction means may also be an acoustic speaker, gas mass injection or dilution. A pressure-measuring device 6 is coupled to the combined air cavity and contains transducer, offset, gain, calibration adjustment, and other instrumentation components common to the industry. Operation of the embodiment shown in FIG. 1 begins with calibration of pressure-measuring device 6, using calibration equipment and techniques common to the industry. When accomplished, pressure-measuring device 6 will directly assess air pressure in a standard unit of absolute measure, such as centimeters of water.

At the start of the cycle, piston 4 is situated as shown in FIG. 1A, such that a small volume $V_f$ 5 is defined in cylinder 3. The vent valve 7 is initially open such that the pressure of the system is atmospheric. In FIG. 1B, valve 7 is closed and piston 4 is pushed inward. Pressure in the combined cavity is increased from $P_0$ to P by virtue of the piston displacement, according to physical laws governing gas within a closed mass system. In turn, a sympathetic increase in volume, $V_c$ 8, occurs due to the compliance of wall 2 in cavity 1. Volume of the combined air cavity thus changes from $V_0+V_f$ in FIG. 1A to $V_0+V_c$ in FIG. 1B.

If the total change in system volume is known, the volume $V_0$ can be computed from Boyle's gas equation, $V_0=\Delta V[P_0/(P-P_0)]$ where $\Delta V=V_f-V_c(P/P_0)$. In a non-compliant system, $V_c=0$, $\Delta V=V_f$, and the original volume $V_0$ can be directly determined. In a compliant system, however, $V_c \neq 0$, and the value for volume obtained by directly applying the gas equation is incorrect. Since $V_c$ is unknown, sufficient information is yet unavailable to determine $V_0$ directly whenever compliance is present in the system.

Figure 1C:
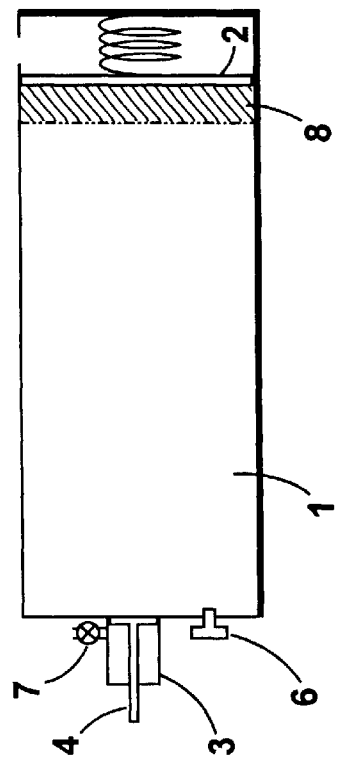
Figure 1B:
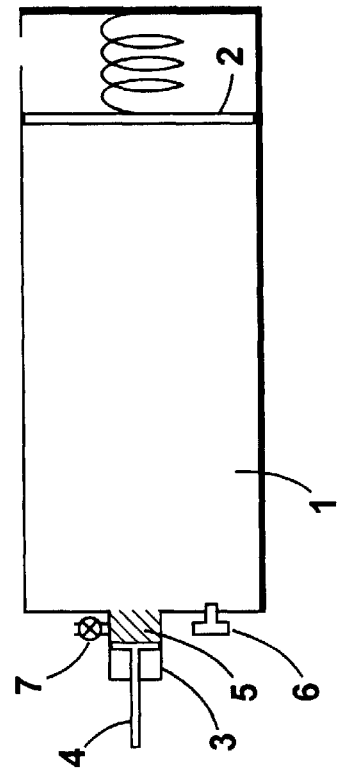
Figure 1D:
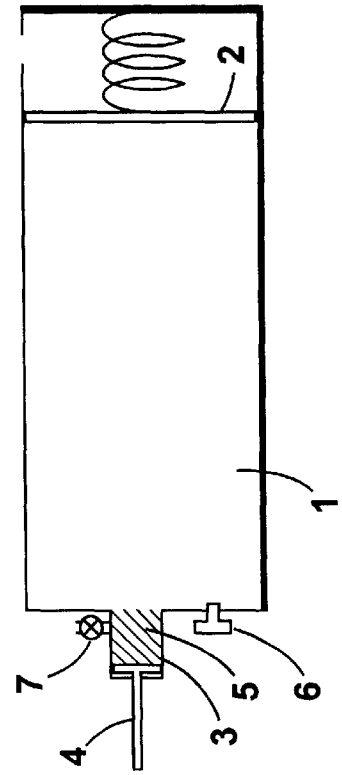

In order to determine if compliance is present in the volume under test, the cycle is repeated using a different piston chamber volume $V_f' \neq V_f$ (FIGS. 1C and 1D). The mass of the system has now changed so that the gas equation results in an independent system equation from which volume can again be computed from the new measured change in pressure $P'-P_0$. In the event that the computed volume is different than that calculated from performing the previous maneuver, compliance has been determined to exist and contributions to the system volume due to $V_c$ must be acknowledged.

Although neither $V_c$ or $V_c'$ is known, compliance may be assumed linear when changes in pressure occur that are small relative to atmospheric. In other words, a compliance parameter C may be defined, where $V_c=C(P-P_0)$ and $V_c'=C(P'-P_0)$. Thus, the two independent system equations can be written in terms of $P_0$, P, P', $V_f$, $V_f'$, C, and $V_0$, where the first five of these terms are known by way of measurement and the latter two are the unknown parameters of the system. By techniques familiar to those skilled in the art, C and $V_0$ can be determined by various numerical means, including methods of linear diagonalization and methods of variance, depending upon the degree of sensitivity among terms.

The volume of air 1 in FIG. 1A is at a constant (body) temperature prior to the movement of piston 4 in FIG. 1B. Small changes in gas temperature occur due to movement of piston 4 because of gas compression. The effect of temperature change can be neglected whenever sufficient time is allowed for temperature of the gas to dissipate in the tissues of the body prior to pressure data collection. In the case of in vivo volumes such as lung, this time period is very short (less than 500 ms) due to the large surface area and efficient heat transfer characteristics of lung tissue. Alternately, if rapid sampling is required, such as for purposes of data averaging, effects of temperature may be accommodated by including temperature terms into the general gas equation, $P_0(V_0+V_f)/T_0=P(V_0+V_c)/T$, where temperature is measured by a transducer with a sufficiently high frequency response and sensitivity adapted into pressure transducer 6.

Operation of a typical embodiment of the apparatus shown in FIG. 2 begins with calibration of pressure transducer 24 as described above. The apparatus is interfaced to the patient, with face mask 20 forming an airtight seal between the inner cavity of the apparatus 21 and in vivo air volume of the patient. This results in a combined air cavity of yet unknown volume, $V_0$. Normal breathing by the patient is vented through valve 22. The valve interfaces between the external environment and the inner cavity of the apparatus, and is opened or closed by passive means according to breathing pressure of the patient. The valve is constructed in such a manner as to remain open while the patient is in the process of inhaling or exhaling and to momentarily close during the time the patient is changing breathing modality from exhalation to inhalation, when cavity pressure is beneath the shutter threshold. The pressure change in the system due to the induced change in volume is, in itself, insufficient to open the valve.

The processing and control unit 23 monitors the pressure of the system via pressure transducer 24, which will be atmospheric at the trough of the breathing cycle. At that moment, the passive valve is closed, sealing the system. The processing and control unit (PCU) signals linear motor 25 to move piston 26 a calibrated amount, inducing a volume change in the system by an amount $V_f$ 27. After a suitable settling time, PCU 23 measures the system pressure via transducer 24. This procedure provides measures of $V_f$, $P_0$, P and a preliminary estimate for $V_0$ as described in previous paragraphs.

The sequence is repeated except that PCU 23 causes piston 26 to induce a different volume $V_f'$. PCU 23 thus obtains additional measures of $V_f'$, $P_0$, P' and a second estimate for $V_0$ to determine (a) if compliance exists in the system and (b) measures of $V_0$ and the compliance parameter C as described above. Calculated values for $V_0$ and C are displayed by a digital display unit on PCU 23. Several breath cycles may be monitored for purposes of averaging.

In a practical application of the apparatus, when measuring complex and dynamic volumes such as the human lung, sources of artifact, in addition to that introduced by compliance, are often problematic. One potential problem is associated with the small changes in lung volume that eventuate by blood being forced into the lung by the heart. Although this volume change is very small in relation to the volume of the lung, it may be appreciable in relation to the volume change induced to the system by the apparatus by which measures are obtained. The volumetric action of the heart on the lung wall creates a similar source of change in system pressure. FIG. 3 shows an alternative embodiment of the invention with components added which address these physiologic phenomena.

A valve 30 controlled by PCU 23 replaces passive valve 22 shown in the embodiment of FIG. 2. A control signal from PCU 23 signals the valve to vent the apparatus cavity to atmosphere when a preset differential pressure between system and atmosphere exists. A pneumotach screen 31 provides a small resistance to airflow in and out of the mask to allow transducer 24 in conjunction with PCU 23 to monitor flow and thus control valve 30 as noted. Utilization of an active valve in the alternative embodiment of the apparatus facilitates management of the system measuring process and provides surety to PCU 23 about valve status.

At the trough of the breathing cycle, control signals from PCU 23 close valve 30 and signal motor 25 to drive piston 26 in such a manner to induce a known increase to system volume. This increase results in a decrease in pressure of the system, instead of an increased pressure as in the case of the previous embodiment. Utilizing a reduced system pressure in the alternative embodiment reduces the tendency for involuntary glottal closure that might otherwise result due to excitation of supralaryngeal baroreceptors during pressurization.

A pulse monitoring means, provided by a pulse monitor 33, allows each induced volume change to occur at the same phase in the heart cycle, thereby reducing the volume artifact caused by blood flow into and out of the lung and the artifact generated by the heart pushing on the wall of the lung. The total system pressure is monitored by transducer 24 and processed by PCU 23 such that slowly-varying pressure artifacts induced by the sources described above can be reduced either by filtering or by providing control feedback to piston 26 in such a manner to continually move it in a fashion to oppose pressure artifacts.

A glottal monitoring means, provided by the glottal monitor 32 (an electroglottograph or similar device), monitors the status of the glottis to determine which volume is being measured. When the glottis is closed, the volume being measured is that of the pharnyx. A nasal mask can replace the facemask for use in measuring the nasal pharynx, and the difference between the two measures provides the volume of the orapharynx. For this measurement, the patient's velum must be closed as occurs during swallowing.

In addition to measuring volumes of these cavities, taking volume measurements of the lung at the peak of the breathing cycle provides PCU 23 with information required to determine spirometric measures such as functional expired volume (FEV) in addition to the volume obtained at the trough of the breathing cycle, which is functional residual capacity (FRC).

Calibration of the pneumotach formed by the resistance screen 31 located in valve 22 permits measures of volumetric air flow by PCU 23, thus facilitating averaging of calculated in vivo volume measurements obtained over successive breathing cycles.

The specific embodiments herein disclosed are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An apparatus for measuring gas volumes of a cavity of unknown compliance in a subject having a heart cycle comprising,:
   (a) an air cavity with induction means for inducing calibrated mass and volume changes in said air cavity;
   (b) a means for interfacing said air cavity to said subject;
   (c) a means for interfacing said air cavity to the volume to be measured;
   (d) a means of interfacing said air cavity to ambient environment to facilitate ordinary breathing activity of said patient during measurement;
   (e) a means for measuring air pressure variations in said air cavity;
   (f) a processing means electrically coupled to said induction means;
   (g) a means for monitoring pulse, wherein said means allows each induced volume change to occur at the same phase in the heart cycle and wherein said means is coupled to said processing means and
   (h) measuring means for calculating the gas volume.

2. The apparatus of claim 1, wherein the gas volumes are in vivo lung, thorax, orapharynx, and/or nasopharynx volumes of a human patient.

3. The apparatus of claim 1, wherein the means for interfacing said air cavity to the ambient environment is a respiratory valve.

4. The apparatus of claim 1, wherein the induction means is a piston, acoustic speaker, or gas mass injection or dilution.

5. The apparatus of claim 1, wherein the interface to the subject is a facial mask, mouthpiece, nasal mask or tubes.

6. The apparatus according to claim 1, which further comprises a glottal monitoring means.

7. The apparatus according to claim 1, which further comprises a means for measurement of volumetric air flow during breathing.

8. An apparatus for measuring gas volumes of a cavity of unknown compliance in a subject comprising:
   (a) an air cavity with induction means for inducing calibrated mass and volume changes in said air cavity;
   (b) a means for interfacing said air cavity to said subject;
   (c) a means for interfacing said air cavity to the volume to be measured;
   (d) a means of interfacing said air cavity to ambient environment to facilitate ordinary breathing activity of said patient during measurement
   (e) a means for measuring air pressure variations in said air cavity;
   (f) a processing means electrically coupled to said induction means;
   (g) a glottal monitoring means and
   (h) measuring means for calculating the gas volume.

9. The apparatus of claim 8, wherein the gas volumes are in vivo lung, thorax, orapharynx, and/or nasopharynx volumes of a human patient.

10. The apparatus of claim 8, wherein the means for interfacing said air cavity to the ambient environment is a respiratory valve.

11. The apparatus of claim 8, wherein the induction means is a piston, acoustic speaker, or gas mass injection or dilution.

12. The apparatus of claim 8, wherein the interface to the subject is a facial mask, mouthpiece, nasal mask or tubes.

13. The apparatus according to claim 8, which further comprises a means for monitoring pulse, wherein said means is coupled to said processing means for coordinating volume measurements with the heart cycle.

14. The apparatus according to claim 8, which further comprises a means for measurement of volumetric air flow during breathing.

15. A method for measuring a gas volume of a cavity having compliance in a subject comprising:

(a) attaching an apparatus to said cavity, said apparatus comprising: (i)an air cavity with induction means for inducing calibrated mass and volume changes in said air cavity; (ii) a means for interfacing said air cavity to said subject; (iii) a means for interfacing said air cavity to the volume being measured; (iv) a means for interfacing said air cavity to ambient environment to facilitate ordinary breathing of said patient during measurement; (v) a means for measuring air pressure variations within said air cavity; (vi) a processing means electrically coupled to said induction means; (vii) a means for calculating said gas volume;

(b) measuring the barometric pressure in an area near the subject;

(c) measuring the change in induced pressure and volume in said cavity during at least two inductions;

(d) calculating compliance of said cavity, and (e) calculating said gas volume.

16. The method of claim 15, where the said cavity is the in vivo thoracic, orapharynx, nasopharynx and lung cavities.

17. The method of claim 15, which further comprises averaging volume measurements obtained over successive breathing cycles.

18. A method for measuring a gas volume of a cavity having compliance in a subject comprising:

(a) attaching an apparatus to said cavity, said apparatus comprising: (i) an air cavity with induction means for inducing calibrated mass and volume changes in said air cavity; (ii) a means for interfacing said air cavity to said subject; (iii) a means for interlacing said air cavity to the volume being measured; (iv) a means br interlacing said air cavity to ambient environment to facilitate ordinary breathing of said patient during measurement; (v) a means for measuring air pressure variations within said air cavity; (vi) a processing means electrically coupled to said induction means; (vii) a means for calculating said gas volume;

(b) measuring barometric pressure in an area near the subject;

(c) measuring the change in induced pressure and volume in said cavity during at least three inductions of varying rates and volumes at similar glottal configurations and heart cycle times;

(d) calculating airway resistance to said volume;

(e) calculating compliance of said cavity, and (f) calculating said gas volume.

* * * * *